*(12)* United States Patent
Frech et al.

(10) Patent No.: US 10,343,998 B2
(45) Date of Patent: Jul. 9, 2019

(54) SYNTHETIC PATH TO PHARMACEUTICALLY ACCEPTABLE VISMODEGIB

(71) Applicant: AZAD PHARMACEUTICAL INGREDIENTS AG, Schaffhausen (CH)

(72) Inventors: Christian Manfred Frech, Bertschikon (CH); Pasquale Gabriele Grieco, Corsico (IT); Christine Aebersold, Uster (CH); Patrick Müller, Römerswil (CH); Jan-Erik Ingenhoff, Horgen (CH); Miriam Oberholzer, Beringen (CH); Viktorya Rstakyan, Yerevan (AM); Roman Gerber Aeschbacher, Frauenfeld (CH)

(73) Assignee: AZAD PHARMACEUTICAL INGREDIENTS AG, Schaffhausen (CH)

( * ) Notice: Subject to any disclaimer, the term of this patent is extended or adjusted under 35 U.S.C. 154(b) by 0 days.

(21) Appl. No.: 15/935,558

(22) Filed: Mar. 26, 2018

(65) Prior Publication Data

US 2018/0273477 A1    Sep. 27, 2018

(30) Foreign Application Priority Data

Mar. 27, 2017 (GB) .................................. 1704801.8

(51) Int. Cl.
*C07D 213/40* (2006.01)
*C07D 213/56* (2006.01)

(52) U.S. Cl.
CPC ......... *C07D 213/40* (2013.01); *C07D 213/56* (2013.01)

(58) Field of Classification Search
CPC ............................ C07D 213/40; C07D 213/56
See application file for complete search history.

(56) References Cited

FOREIGN PATENT DOCUMENTS

| EP | 0179239 A2 | 4/1986 |
|---|---|---|
| EP | 0372934 A2 | 6/1990 |
| WO | 2006028958 A2 | 3/2006 |
| WO | 2009126863 A2 | 10/2009 |

OTHER PUBLICATIONS

Gorlitzer, Klaus. Archiv der Pharmazie (Weinheim, Germany) (1992), 325(6), 357-9.*
Sharma, Rohit. Chem. Commun. (2016) 52, 1009.*
Ohkura, Kazue. Chem. Pharm. Bull 41(11) 1920-1924 (1993).*
Schofield, K. et al, "The nitration of heterocyclic nitrogen compounds", Quarterly Reviews, Chemical Society, vol. 4, 1950; pp. 382-403.
Forsyth, R. et al, "CCCLXXXVIII.Nitration of 2-, 3-, and 4-phenylpyridines", Quarterly Reviews, Chemical Society, vol. 4, 1950; pp. 2912-2924.

* cited by examiner

*Primary Examiner* — Emily A Bernhardt
*Assistant Examiner* — Laura M Daniel
(74) *Attorney, Agent, or Firm* — Harness, Dickey & Pierce, P.L.C.

(57) ABSTRACT

The present invention relates to a new route of synthesis to obtain pharmaceutically acceptable Vismodegib. In addition, besides the synthesis also suitable pharmaceutical compositions and the use of the compound for the treatment of basal-cell carcinomas are disclosed.

9 Claims, 1 Drawing Sheet

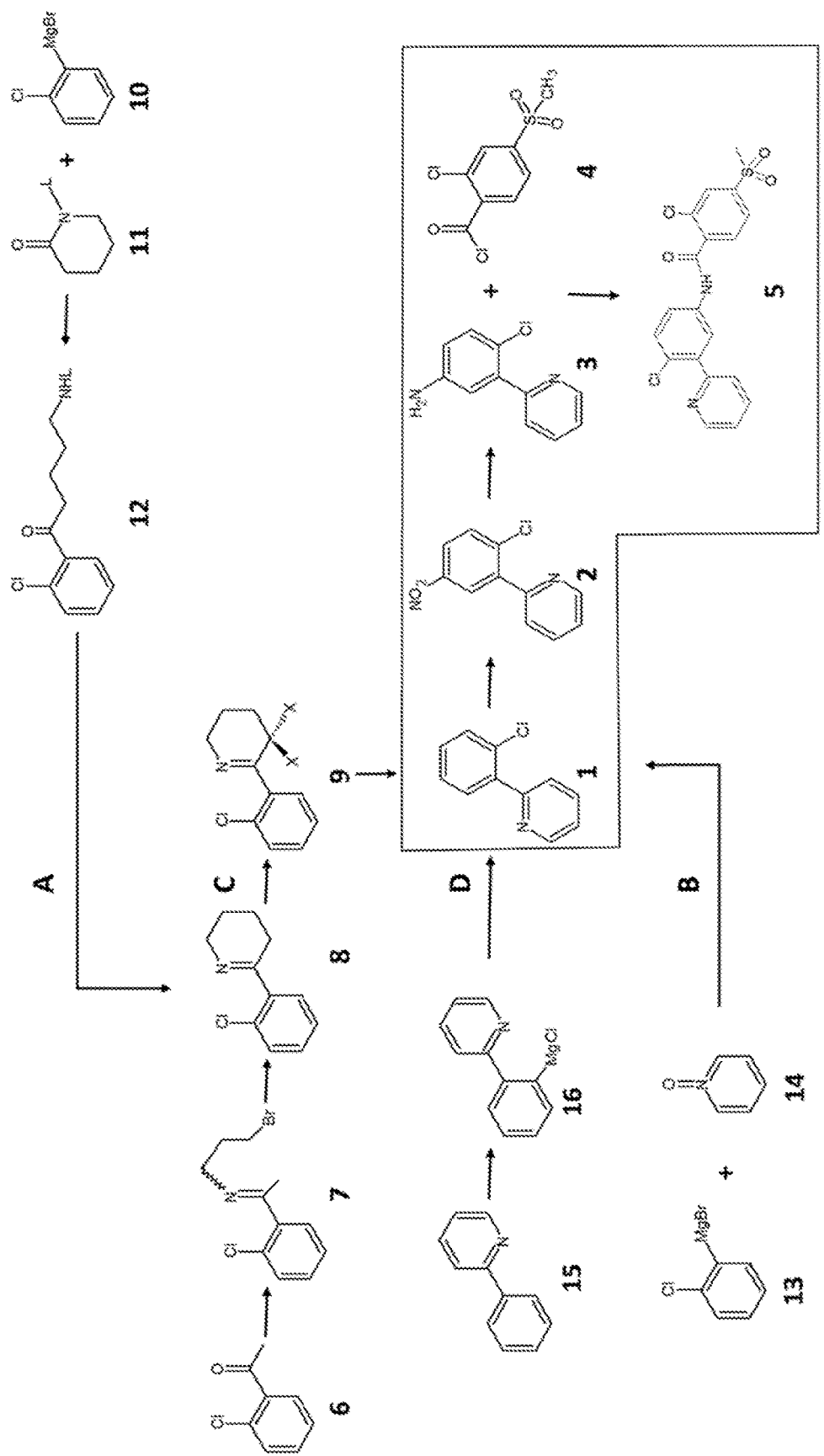

SYNTHETIC PATH TO PHARMACEUTICALLY ACCEPTABLE VISMODEGIB

FIELD OF THE INVENTION

The present invention relates to a new route of synthesis to obtain pharmaceutically acceptable Vismodegib. In addition, besides the synthesis also suitable pharmaceutical compositions and the use of the compound for the treatment of basal-cell carcinomas are disclosed.

BACKGROUND

Vismodegib belongs to the chemical class of pyridyl-compounds and is represented by the following chemical formula I Formula I The compound is known for being an active pharmaceutical ingredient targeted to inhibit the hedgehog signaling pathway and is marketed for the treatment of hyperproliferative/angiogenesis mediated diseases like basal cell carcinoma (BCC) or metastatic basal cell carcinoma (mBCC).

One way of Vismodegib synthesis is for instance disclosed in WO 2006/028958 A2. Furthermore, besides the compound itself also patent literature is available, disclosing several co- and multi-component crystals of Vismodegib (e.g. WO 2016/020324 A1).

Nevertheless, besides the known processes for the synthesis of Vismodegib there is still the need for reliable and easy alternatives based on purely organic synthesis steps and omitting the need of heavy metal-based synthesis steps.

BRIEF DESCRIPTION OF THE INVENTION

Above mentioned problem is solved by a process for the preparation of Vismodegib (2-chloro-N-(4-chloro-3-(pyridin-2-yl)phenyl)-4-(methylsulfonyl)-benzamide), wherein the process at least comprises the steps of reacting compound (1) (2-(2-chlorophenyl)pyridine) in the presence of nitric acid to give compound (2) (2-(2-chloro-5-nitrophenyl)pyridine),

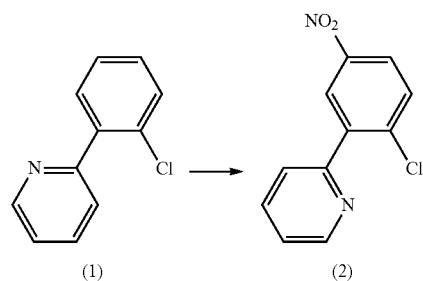 [SMILES: Clc1ccccc1-c1ccccn1 ; O=[N+]([O-])c1ccc(Cl)c(-c2ccccn2)c1]

reducing compound (2) (2-(2-chloro-5-nitrophenyl)pyridine) to give compound (3) (4-chloro-3-(pyridin-2-yl)aniline)

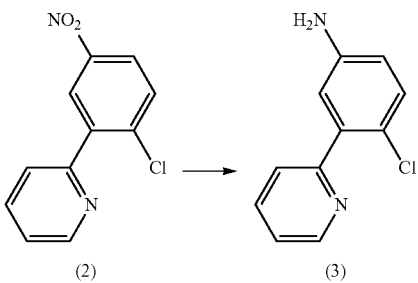 [SMILES: O=[N+]([O-])c1ccc(Cl)c(-c2ccccn2)c1 ; Nc1ccc(Cl)c(-c2ccccn2)c1]

and reacting compound (3) (4-chloro-3-(pyridin-2-yl)aniline) and compound (4) (2-chloro-4-(methylsulfonyl)benzoyl chloride) to give compound (5) (Vismodegib)

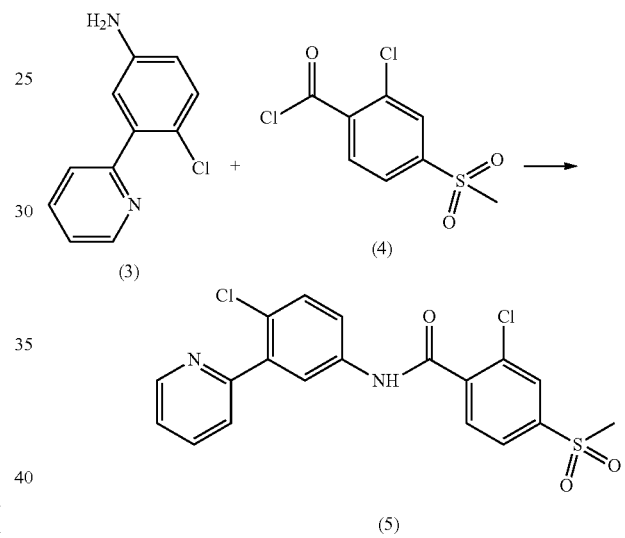

Surprisingly it was found, that above described process steps can be used to reproducibly synthesize compound (5) at high purity and only small amounts of by-products, which can easily be separated from the main compound Vismodegib. Especially, it is also possible to follow that route without the need of pharmaceutically unsuitable substances, like e.g. the need of heavy metals, up to the reducing step. This advantage is not known from the state of the art, wherein always heavy metal catalyzed C—C coupling is proposed for building the aromatic ring structure. Therefore, the achievable Vismodegib is especially suited for being used in pharmaceutical compositions, because the heavy metal content of such compositions can be lower compared to the state of the art processes. In addition, the technical process is easy up-scalable, because reliable and reproducible crystallization and filtration steps are disclosed. Furthermore, the reaction temperature is limited for all steps below 80° C. Therefore, in comparison to state of the art processes only a small amount of unwanted by-products is generated during synthesis.

In a first reaction of the inventive route of synthesis compound (1) (2-(2-chlorophenyl)pyridine) is reacted in the presence of nitric acid to give compound (2). The nitration of the aromatic ring structure comprising the halide may suitably be achieved by contacting compound (1) with an inorganic nitric acid salt in the presence of a concentrated acid like conc. $H_2SO_4$. Preferably, the alkali salt used for this nitration step is the potassium salt $KNO_3$.

In a next step compound (2) (2-(2-chloro-5-nitrophenyl) pyridine) is reduced to give compound (3) (4-chloro-3-(pyridin-2-yl)aniline). The reduction of the nitro-group can be performed in the presence of inert solvents like alcohols and is preferably performed in ethanol. The selectively reduction of the aromatic nitro groups may be performed in the presence of metal salt like for instance Tin(II)chloride. Other suitable reducing agents may be selected from the group consisting of elemental Sn, Zn or Fe in HCl, or Ni, Pt or Pd with $H_2$. Furthermore, sodium hydrosulfite, sodium sulfide or titanium (III) chloride are suitable to reduce aryl nitro compounds to anilines.

Finally, the proposed route of synthesis includes reacting compound (3) (4-chloro-3-(pyridin-2-yl)aniline) and compound (4) (2-chloro-4-(methylsulfonyl)benzoyl chloride) to give Vismodegib. This last synthesis step can for instance be performed in an inert solvent like THF and is preferably in a temperature range from −10° C. up to 10° C. The reaction can be started by the addition of a base, like a tertiary amine. Preferably $NEt_3$ can be used for the reaction. The reaction time is suitably in the range of 10-20 h and after the reaction is finished the organic solvent is evaporated. For purification purposes the product can be suspended in an aqueous solution of weak alkali bases like $NaHCO_3$ and extracted by an organic solvent like dichloromethane (DCM). After removal of the organic solvent the product can be further purified by known procedures, like column chromatography or recrystallization.

In a preferred embodiment of the invention the compound (1) (2-(2-chlorophenyl)pyridine) is synthesized from educts comprising no pyridine-ring. This means, that the starting educt for the synthesis may already comprise an aromatic ring structure. Therefore, the need to synthesize this ring structure by heavy metal catalyzed ring formation is avoided. The synthetic steps are directed to build the heteroatom containing aromatic ring. These steps can be achieved much easier at high yields and in the absence of heavy metal catalysts, which are usually used for C—C ring formation. In consequence, an easier and less toxic process is suggested, wherein also the metal content in the final product is reduced compared to synthesis strategies, which are directed to build the aromatic C—C ring.

In a further characteristic compound (1) (2-(2-chlorophenyl)pyridine) can be obtained by reacting compound (6) (2-chloroacetophenone) and 3-Y-propylamine, wherein Y is selected from the group consisting of halogen, OH, SH, $NH_2$, $NR_2$, $PR_2$ to yield the acyclic imine compound (7)

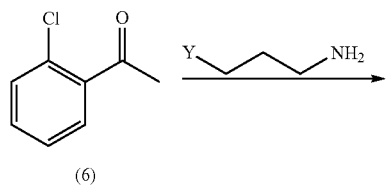

(6)

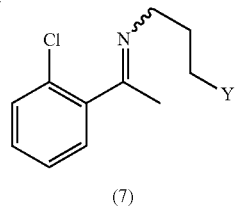

(7)

followed by a reaction in the presence of a base to yield the cyclic imine compound (8)

(7) → (8)

and halogenating compound (8) to yield the di-halo compound (9), wherein X=Cl, Br, I (8) → (9)

followed by aromatization in the presence of a base to yield compound (1). This reaction scheme is able to provide compound (1) in high yields, at high selectivity and without using unwanted, hard to remove process chemicals. The pyridine ring structure is generated by addition of a further functionalized propylamine to the exo-ketone moiety. Within this step an imine is formed at least as an intermediate. This reaction may either be performed in a one-step synthesis for instance using the diamine dissolved in DMSO in the presence of catalytic amounts of iodine, HCl and oxygen or by using a two-step synthesis. The two-step synthesis being preferred, because by choosing this route higher yields are obtainable and the generated by-products, if any, are easily separable from the main product at moderate processing temperatures.

The two-step synthesis may include a first reaction of the ketone with a halo-functionalized amine in dry organic solvents in the presence of a side-group metal catalyst and weak to moderate organic bases like tertiary amines. The ring closure of the imine compound is afterwards achieved base catalyzed. For the base catalyzed step strong organic bases like lithiumdiisopropylamide BuLi, Hexamethyldisilazane (HMDS) Lithium salt may be used. This two-step reaction especially results in high yields at moderate processing times.

In another aspect of the invention, the first reaction step in above given reaction scheme, i.e. the reaction of compound (6) to compound (7), can be performed in the presence of dimethylformamide (DMF), dichloromethane (DCM), $TiCl_4$ and trimethylamine ($Et_3N$). Especially the combination of the Ti-metal catalyst and the aprotic dry organic solvents result in high yields and fast reactions. This effect may, at least in part, be based on the fact that DMF does not solubilize the Et₃NHBr salt and, therefore, shifting the reaction equilibrium to the product. In addition, a large excess of triethylamine (ratio trimethylamine:educt may be larger or equal than 10) can be used if very high yields and a high purity is needed, because at high ratios the tar formation is reduced.

In another characteristic in the above disclosed reaction scheme the di-halogenation step, i.e. the reaction of compound (8) to compound (9), can be performed in the presence of N-Chlorosuccinimide (NCS) and the molar ratio of the NCS to the educt (NCS:educt) can be larger or equal to 4. Furthermore, the molar ratio of NCS to the educt (NCS:educt) can be larger or equal to 5 and preferably larger or equal to 6. Within these reaction conditions high reaction rates are obtainable in the halogenation. Furthermore, this reaction is very stereo-specific, reducing the generation of unwanted by-products, leading to high yields.

In another aspect compound (1) (2-(2-chlorophenyl)pyridine) can be obtained by reacting compound (10) ((2-chlorophenyl)-M-bromide), wherein M is Mg or Ca, and compound (11) (N-protected delta-Valerolactam), wherein L is a protection group to give compound (12) (5-L-amino-1-(2-chlorophenyl)pentan-1-one)

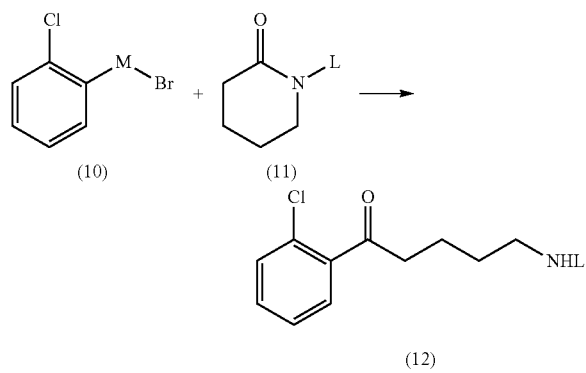

followed by de-protection of compound (12) to give bi-cyclic compound (8)

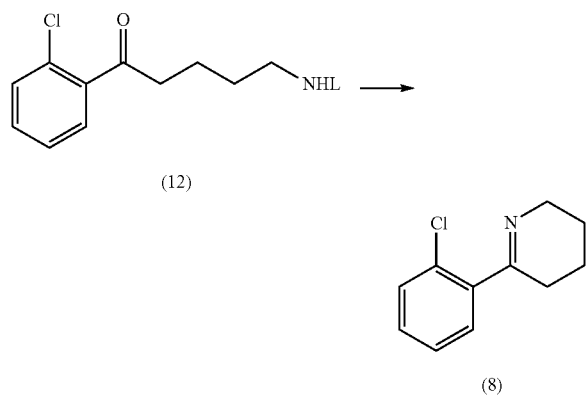

which is further halogenated to yield the di-halo compound (9), wherein X=Cl, Br, I

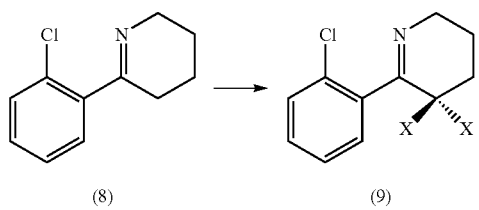

followed by aromatization of compound (9) in the presence of a base to yield compound (1). It is also within the scope of the invention to achieve the ring formation of the pyridine ring by using a lactam-educt. Also this reaction route results in high yields and low processing times. Within the first step a Mg- or Ca-Grignard-compound may be used in order to achieve the coupling of the N-protected lactam. Preferably this reaction can be performed in the further presence of a LiCl-compound, wherein especially LiCl is able to speed up the reaction by enhancing the nucleophilicity of the aromatic carbon. Suitable protection groups may be selected from the group consisting of BOC, Cbz, FMoc, acetyl (Ac), benzoyl (Bz), p-methoxybenzyl carbonyl (Moz), benzyl (Bn), carbamate, tosyl (Ts), trichloroethyl chloroformate (Troc). After the addition of the lactam under ring-opening the N-protecting group may be removed by known chemical means. Preferably this de-protection step is performed in the absence of any solvent. For instance, water would prolong the reaction time and would decrease the overall yield by negatively influencing the condensation step and the recovery of the products during the work-up. The last step of di-halogenation of the compound (8) may be achieved in a similar fashion as described above. Within this route of synthesis high yields are achievable.

In a further aspect the aromatization step in above given reaction scheme, i.e. the reaction from compound (9) to compound (1), can be performed in the presence of a polar aprotic solvent and a base, wherein the base is selected from the group consisting of potassium bis(trimethylsilyl)amide, lithium diisopropylamide (LDA), caesium carbonate, caesium bicarbonate, potassium carbonate, sodium carbonate, potassium bicarbonate, sodium bicarbonate, t-BuOK, NaOEt, NaOMe or mixtures thereof. Suitable solvents may be selected from the group consisting of CH₃CN, THF, Chloroform, DCM, DMSO, DMAc, MeOH or mixtures thereof. Within these reaction conditions a complete aromatization can be achieved at very short reaction times. In addition, NaOMe in Methanol is preferred, because under certain conditions the reaction of compound (8) to compound (9) may generate an un-identified process impurity, which has to be separated in an additional step from the desired product. If in this reaction step a MeOH/NaOMe combination is used this impurity is fully purged and no additional purification is required. Therefore, the overall synthesis and purification route can be shortened and rendered more efficient.

In another preferred aspect compound (1) (2-(2-chlorophenyl)pyridine) can also be obtained by reacting compound (10a) ((5-R-2-chloro-phenyl)-M-bromide), wherein M is Mg or Ca and R is a protection group and compound (11) (N-protected delta-Valerolactam), wherein L is a protection group to give compound (12a) (5-L-amino-1-(5-R-2-chlorophenyl)pentan-1-one)

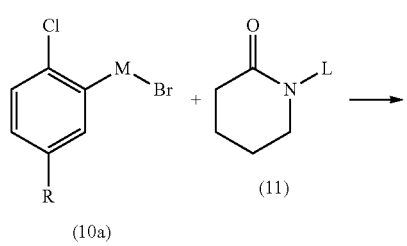

(10a)     (11)

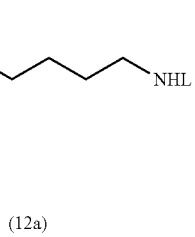

(12a)

followed by single or double de-protection of compound (12) to give bi-cyclic compound (8)

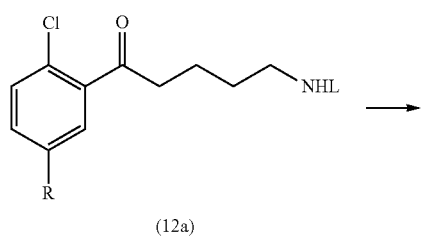

(12a)     (8)

which is further halogenated to yield the di-halo compound (9), wherein X=Cl, Br, I.

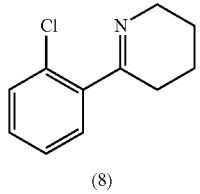

(8)     (9)

followed by aromatization in the presence of a base to yield compound (1). It is also possible to perform the reaction as described above, wherein both educts are carrying protecting groups. This may further enhance the selectivity of the reaction and improve the yield.

Within a preferred embodiment of the invention group R in compound (10a) can be Me$_2$SiCH$_2$CH$_2$SiMe$_2$. Especially this bulky protecting group may be able to further increase the selectivity of the reaction.

In a further preferred characteristic the compound (1) (2-(2-chlorophenyl)pyridine) can be synthesized from at least one educt comprising a pyridine-ring. Within this embodiment no heavy metals are necessary in order to build the ring-structure. Therefore, the overall heavy metal content in the product is further reduced compared to state of the art synthesis.

In another embodiment the compound (1) (2-(2-chlorophenyl)pyridine) can be obtained by reacting compound (13) ((2-chlorophenyl)magnesiumbromide) and compound (14) (pyridine N-oxide) to yield compound (1)

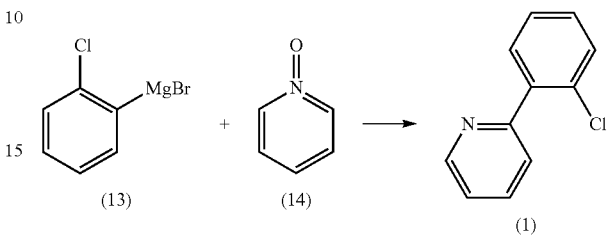

(13)     (14)     (1)

This reaction can preferably be performed in the presence of an organic aprotic solvent like THF, DMF, DMSO, DMAc, Toluene, Dioxane, ethyl acetate or the like.

In a further characteristic the reaction of compound (13) and compound (14) in above displayed reaction can be performed in boiling acetic acid anhydride (Ac)$_2$O. Especially the use of acetic acid anhydride may positively influence the overall yields and reduce the amount of un-wanted by-products. It is also possible to perform the reaction in other solvents, like acetyl chloride or other anhydrides.

Within a preferred aspect compound (1) (2-(2-chlorophenyl)pyridine) can be obtained by reacting compound (15) (2-phenylpyridine) in the presence of a Grignard-reagent to yield compound (16) (2-(2-Magnesiumchlorophenyl)pyridine)

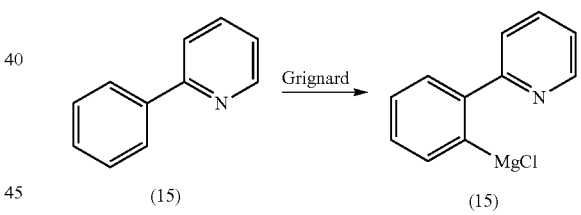

(15)     (15)

and further reacting compound (16) in the presence of a chloride-source to yield compound (1)

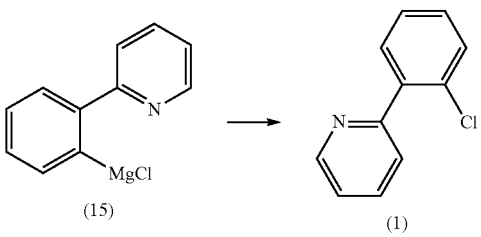

(15)     (1)

Contrary to an electrophilic halogenation of aromatic rings as proposed in the state of the art for the synthesis of Vismodegib this reaction is able to provide higher yields. Furthermore, the reaction temperature is lower, resulting in a better process control and a reduced amount of unwanted side-products.

In another aspect of above displayed reaction scheme, i.e. the reaction of compound (15) to compound (16), the Grignard-reagent can be 2,2,6,6-Tetramethylpiperidinyl-magnesium chloride lithium chloride. By using especially this Gringnard-compound it is possible to achieve the desired reaction at high selectivity and at high yields.

It is another object of the present invention to disclose a pharmaceutical composition comprising Vismodegib prepared according to the invention. Within a pharmaceutical composition Vismodegib may be at least one of the APIs (active pharmaceutical ingredient). Furthermore, suitable pharmaceutically acceptable excipients can be present in the composition. Examples for suitable excipients include antioxidants, binders, buffering agents, bulking, agents, disintegrants, diluents, fillers, glidants, lubricants, preservatives, surfactants and co-surfactants.

In another aspect of the invention the disclosed pharmaceutical composition including the inventively synthesized Vismodegib can be used for the treatment of basal-cell carcinomas.

BRIEF DESCRIPTION OF THE DRAWINGS

FIG. 1 displays a schematic diagram of the route of Vismodegib synthesis. The central part exhibits the synthesis of Vismodegib starting from compound (1). Within the disclosure of this FIGURE four different routes (A-D) are given in order to obtain compound (1) at high yields and in a pharmaceutically acceptable quality. All routes have in common that contrary to the state of the art no heavy metal salts are used in the synthesis steps for building C—C ring structures.

EXPERIMENTAL EXAMPLES

I. Synthesis According to Route A

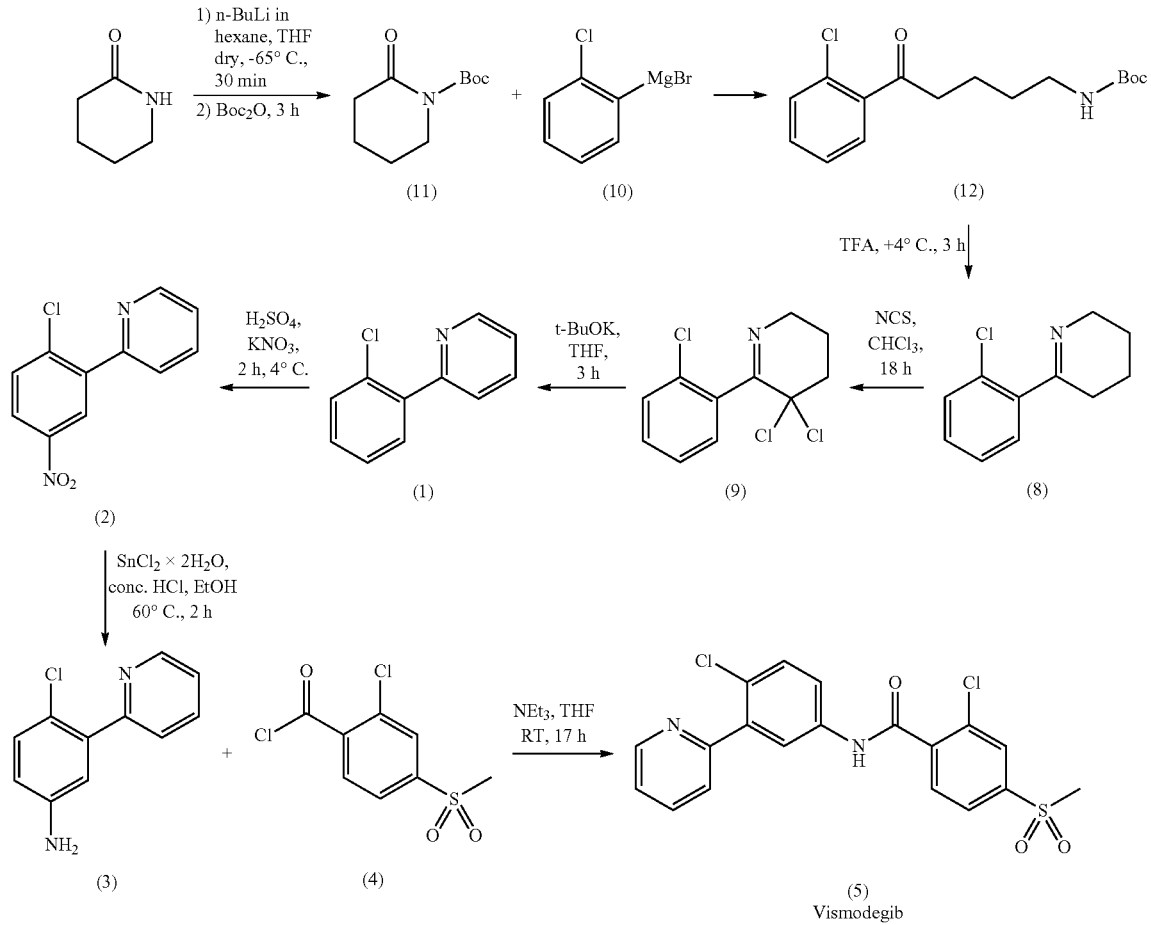

The pharmaceutical composition comprising the inventively synthesized Vismodegib may be an oral dosage form. Especially the inventively synthesized Vismodegib is suitable for being processed into oral dosage forms. This suitability can be especially be addressed to the low heavy metal content, because within the overall process no such substances are utilized. This finding is in contrast to state of the art routes of synthesis, always comprising process steps including heavy metal salts.

Preparation of the (2-chlorophenyl)magnesium bromide (10)

In an oven dried 250 mL double neck round bottomed flask fitted with: nitrogen inlet, silicon septum and magnetic bar, under nitrogen, was placed the 1-bromo-2-chlorobenzene (98.86 mmol, 11.67 mL) and the flask was put in an ice-water bath (+4° C.). Then first a 1.3 M solution of isopropylmagnesium chloride lithium chloride complex solution in THF (25 mL, 32.5 mmol) and then a solution of isopropylmagnesium chloride in THF were added dropwise (1 drop every 2 seconds) through a syringe mounted on a syringe pump. The grey suspension was stirred at room temperature for 180 minutes. After the allotted time the GC-MS analysis of a quenched portion of the Grignard showed just the presence of chlorobenzene.

1-N-Boc-2-piperidone (11)

In an oven-dried 1 liter three necked round bottom flask fitted with: a stirring bar, a thermometer and a silicon septum, was placed the δ-Valerolactam (10000 mg, 98.86 mmol). An atmosphere of nitrogen was established through three cycles of vacuum/nitrogen. Then THF dry (272 mL) was added via syringe in way to dissolve the lactam. The solution was then cooled down to −65° C. (internal temperature) through an acetone-liquid nitrogen bath and a solution of n-Butyllithium in hexanes (40.4 mL, 101 mmol) was added dropwise through a syringe by means of a syringe pump (rate 1 drop every 2 seconds) keeping the temperature of the mixture in the range [−60 to −65° C.]. After 30 minutes, was added a solution of di-tert-butyl dicarbonate (21794 mg, 98.86 mmol) in THF (35 mL) through a syringe by means of a syringe pump (rate 1 drop every 2 seconds) keeping the internal temperature in the range of −60 to −65° C.

In addition, this reaction can also be performed in a different reaction step. In a three necked round bottom flask fitted with: a stirring bar, a thermometer, and a bubler at 22° C., 1000 mg, (10 mmol) δ-Valerolactam was placed. Then a 0.7M solution of DMAP (60 g 0.4 mmol) in ACN (0.8 mL) was added. To the light-yellow solution (BOC)$_2$O (3260 g 15 mmol) was portion wise added accompanied by gas evolution. After full conversion (stirring at internal temperature 22° C. for 2 h) 10 mL 0.1M HCl aq. solution were added and extracted with dichloromethane (3×20 mL). The organic phase was evaporated. Upon addition of 40 ml hexane and cooling to −30° C. and crystals where formed. Yield 82%. Purity 98%. The advantage of this reaction compared to the reaction mentioned above can be seen in that the reaction is performed at room temperature and that DMAP is easier to handle compared to BuLi. Furthermore, a higher degree of purity is achievable.

Intermediate 12

After 180 minutes of stirring the solution above (11), a solution of (2-chlorophenyl)magnesium bromide (10) in THF (98.86 mmol, 76 mL, preparation described below) was added through a syringe by means of a syringe pump (rate 1 drop every 2 seconds) keeping the internal temperature in the range [−60÷−65° C.]. The mixture so obtained was stirred at −65° C. for further 120 minutes and then the cold bath was removed and the mixture was stirred at room temperature overnight. After the allotted time the flask was cooled down to +4° C. (ice-water bath) and a solution of HCl 1N (300 mL) was added dropwise under vigorous stirring inside the mixture. The suspension was then extracted with diethyl ether (150 mL×4) and the organic phase was washed first with a saturated solution of NaHCO$_3$ (150 mL×1) and finally with a saturated solution of NaCl (150 mL×1). The organic phase so obtained was dried over dry MgSO4 and the solvent removed by rotary distillation. The oil obtained was dried under pump to afford 26200 mg of a light-yellow oil. Yield of intermediate 12: 68%.

Intermediate 8

The yellow oil obtained (intermediate 12) was cooled to +4° C. and then dissolved in trifluoro-acetic acid (70 mL, 905 mmol). The dark mixture was stirred at room temperature for 180 minutes and then the mixture was cooled down to +4° C. and a 32% solution of NaOH in water was added cautiously till pH~10. The light-yellow suspension was then extracted with diethyl ether (150 mL×5) and the reunited organic layers were dried over dry MgSO$_4$. The evaporation of the solvent followed by drying in a high vacuum pump overnight, afforded 13020 mg (67.23 mmol) of a red-brown oil (Yield=68%, MW=193.67).

Alternatively, this reaction can be performed using different reaction conditions. I.e., in an oven dried 1000 mL three neck round bottomed flask fitted with nitrogen inlet, a dropping funnel, a thermometer and magnetic stirring bar, 8000 mg (40 mmol) 1-N-Boc-2-piperidone (11) dissolved in 160 ml THF was added and then cooled to −35° C. A solution of (2-chlorophenyl)magnesium bromide (10) in THF (51.75 mmol, 345 mL, 0.15M) was added through a dropping funnel keeping the temperature in the range of −35÷−40° C. (approx. 4 h.).

After completion of the reaction (HPLC control) to the 450 ml of a 12M HCl solution was added via a dropping funnel allowing the temperature to increase from −40° C. to +22° C. The formed suspension was stirred overnight at room temperature. 1000 ml water where added and extracted with Diethyl ether (3×150 mL). 900 ml Ammonium hydroxide was added to the aqueous phase which was then extracted with diethyl ether (2×100 mL). The obtained organic phase was dried over dry NaSO4 and the solvent removed by rotary distillation. Intermediate 8 was obtained as an oily product (Yield >100%). Within this reaction the first part is performed at −35° C. instead of −65° C. This may increase the reaction speed. In addition, there is no need for isolation of compound (12). The use of NH$_4$OH improves the purity profile significantly and the overall process is more environmentally friendly by the use HCl instead of TFA.

Intermediate 9

In a 500 mL single neck round bottomed flask, to a cooled solution (+4° C.) of 6-(2-chlorophenyl)-2,3,4,5-tetrahydropyridine (10682 mg, 55.15 mmol) (8) in CHCl$_3$ (150 mL) was added portion-wise the N-chlorosuccinimide (45000 mg, 330.2 mmol) and the walls of the flask were washed with further carbon tetrachloride (50 mL). The suspension was stirred overnight at room temperature. Water (100 mL) and a saturated solution of sodium hydrogen carbonate (100 mL) were added to quench the reaction. The phases were separated and the aqueous one was extracted with carbon tetrachloride (150 mL×2). The combined organic phases were dried (dry MgSO$_4$) and evaporated under vacuum giving the wanted product as a yellow solid. (14190 mg, Yield=98%, MW=262.56).

In an alternative route of synthesis this step can also be performed according to: In a 250 mL round bottomed flask, to a solution of 6-(2-chlorophenyl)-2,3,4,5-tetrahydropyridine (5000 mg, 25.47 mmol) (8) in ACN (100 mL) two portions of N-chlorosuccinimide (7300 mg, 55 mmol) dissolved in ACN (200 mL) where added at 22° C. 200 mL ammonium hydroxide where added portion-wise to the light orange solution while the temperature decreased to 12° C. 27000 mg sodium chloride where added to obtain a biphasic system. The water layer was extracted with 100 ml diethylether. The combined organic phases were dried with Na2SO4 and evaporated to yield the product as a brown oil. (4430 mg, Yield=67%). In this step advantageously ACN is used instead of Chloroform. This helps to shorten the reaction time to 30 min instead of approx. 12 h (overnight). In addition, the reaction mixture is present as solution and avoids the formation of a precipitate in Chloroform.

Intermediate 1

In a 500 mL single neck round bottomed flask, at room temperature, to a solution of 5,5-dichloro-6-(2-chlorophenyl)-2,3,4,5-tetrahydropyridine (14190 mg, 54.04 mmol) (9) in THF (80 mL) was added dropwise a solution of potassium tert-butoxide (24750 mg, 216.16 mmol) in THF (170 mL). Then the dark mixture was refluxed for 180 minutes. At the end of the allotted time, water (280 mL) was added to quench the reaction. The mixture was extracted with diethyl ether (150 mL×4) and the organic phase were reunited and dried over dry MgSO4. The evaporation of the solvent and the following drying under high vacuum afforded the wanted product as a brown solid. (8608 mg, Yield=84%, MW=189.64).

It is also possible to perform this step at different reaction conditions. In a 100 mL single neck round bottomed flask, at room temperature, to a solution of 5,5-dichloro-6-(2-chlorophenyl)-2,3,4,5-tetrahydropyridine (2390 mg, 9.1 mmol) (9) in MeOH (65 mL) sodium methoxide (5900 mg, 109.2 mmol) was portion-wise added. Then light brown mixture was refluxed for 180 minutes. At the end of the allotted time, MeOH was distilled off. To the residue was added water (60 mL) and extracted with ethyl acetate (130 mL×3) and the organic phase were reunited and dried over dry $Na_2SO_4$. The evaporation of the solvent and the following drying under high vacuum afforded 1330 mg of the desired product (77%). This step is preferred, because under certain conditions the reaction of compound (8) to compound (9) may generate an un-identified process impurity, which has to be separated in an additional step from the desired product. In this reaction step a MeOH/NaOMe combination is used and this impurity is fully purged and no additional purification is required. Therefore, the overall synthesis and purification route can be shortened and rendered more efficient.

Intermediate 2

In a 500 mL single neck round bottomed flask to a cold (+4° C.) solution of 2-(2-chlorophenyl)pyridine (8608 mg, 45.39 mmol) (1) in $H_2SO_4$ 96% (126 mL) was added $KNO_3$ (4717 mg, 46.65 mmol) in small portion over 5 minutes. The dark mixture was stirred at +4° c. for 120 minutes and then the mixture was poured on ice (0.85 kg) and then neutralized using $K_2CO_3$ till pH-9. To the mixture obtained was added ethyl acetate (400 mL) and the suspension so obtained was filtered (large amount of salts were present). The phases were separated and the aqueous layer was extracted with further AcOEt (150 mL×3). The reunited organic layers were dried over $MgSO_4$. The evaporation of the solvent and the drying under high vacuum afforded the wanted product. (8901 mg, Yield=83%, MW=234.64).

Intermediate 3

In a 500 mL single neck round bottomed flask at room temperature, to a solution of 2-(2-chloro-5-nitrophenyl)pyridine (9151 mg, 1.06 mmol) (2) in EtOH (228 mL) was added tin(II) chloride dehydrate (29254 mg, 127 mmol of $SnCl_2$ dry). Then a solution of HCl 36% (31 mL) in ethanol (31 mL) was added dropwise to the mixture. The solution was stirred 120 minutes at 60° C. Then the solvent was evaporated by means of rotary evaporation and the oil obtained was dissolved in water (400 mL). The mixture obtained was cooled down to +4° C. and basified with NaOH till pH~10. To the suspension was then added AcOEt (300 mL) and the mixture was filtrated and the solid washed with AcOEt (100 mL). The aqueous phase was then extracted with further AcOEt (150 mL×6) and the reunited organic phase were dried (dry $MgSO_4$). The solvent was removed to afford the final product as a brown oil. (6952 mg, Yield=90%, MW=204.66).

Intermediate 4 is Obtained Commercially

Synthesis of Vismodegib (5)

96.3 mg of intermediate 3 (0.471 mmol) has been dissolved in 5 mL THF and the resulting solution was cooled in an ice-bath. To the cooled solution of intermediate 3, a beforehand prepared solution of intermediate 4 (122.4 mg, 0.471 mmol) in 5 mL THF was added. Then, 0.35 mL NEt3 was added to the resulting suspension and the mixture was allowed to stir for 17 h at 0-4° C. After completeness of the reaction, the solvent was evaporated under reduced pressure (rotavap 50° C.) and the residual solid was suspended in 5 mL saturated $NaHCO_3$ solution. Extraction with 3×5 mL of DCM and subsequent evaporation of the organic solvent yielded 194.3 mg of crude Vismodegib (off-white). The crude material was then purified via column chromatography over silica gel, which yielded in 103.5 mg pure Vismodegib (off-white to yellow solid, 52%).

$^1$H-NMR (500 MHz, $CD_2Cl_2$): 9.51 (s, $^1$H), 8.44 (ddd, J=4.9, 1.8 and 1.0 Hz, 1H), 8.01 (dd, J=8.8 and 2.7 Hz, 1H), 7.89 (d, J=1.7 Hz, 1H), 7.74 (dd, J=1.8 and 1.1 Hz, 1H), 7.73-7.71 (m, 2H), 7.86 (dt, J=7.9 and 1.1 Hz, 1H), 7.59 (d, J=8.0, 1H), 7.51 (d, J=8.7 Hz, 1H), 7.22 (ddd, J=7.5, 4.9 and 1.3 Hz, 1H), 2.98 (s, 3H).

II. Synthesis According to Route B

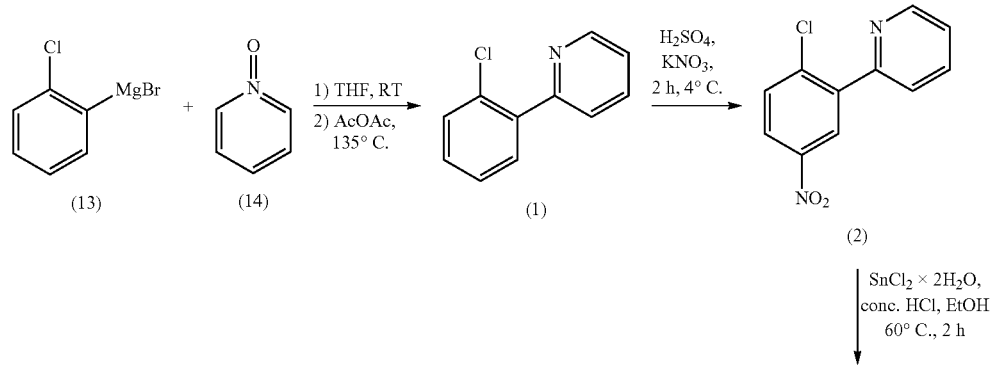

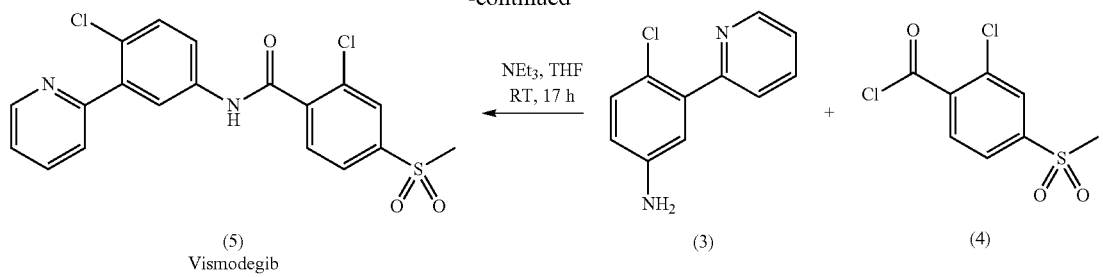

(5) Vismodegib (3)

(4)

Intermediate 1

Under nitrogen, in a dry 250 mL Young-Schlenk, at +4° C. 1-bromo-2-chlorobenzene (1952 mg, 9.99 mmol, 1.19 mL) was added dropwise the isopropylmagnesium chloride lithium chloride complex solution (11.99 mmol, 9.22 mL) and the ice-water bath was removed. The solution was stirred at room temperature until completion of the reaction (4 hours). Then the Grignard was dropped (1 drop every 2 seconds) inside a solution of pyridine N-oxide (1000 mg, 9.99 mmol) (14) in THF (60 mL). The clear solution became a thick orange brown suspension. After the overnight stirring the color of the suspension became light-brown. Water (60 mL) was added to the semisolid mixture together with ethyl acetate (60 mL). The phases were separated and the aqueous one was extracted with further AcOEt (50 mL×3). The organic phases were reunited and dried over dry $MgSO_4$. The evaporation of the solvent left a yellow solid that was dissolved in acetic anhydride (70 mL) and heated at 135° C. overnight. The starting yellow solution switched to dark brown. The mixture was then quenched with ice (100 g) and neutralized with a solution of NaOH 1M until pH-10. The aqueous phase was then extracted with AcOEt (70 mL×3) and the reunited organic phases were washed with further NaOH 1N solution (70 mL) and then dried over dry $MgSO_4$. The evaporation of the solvent left 1567 mg of a brown oil. The crude was purified through a silica column (80 g column, Teledyne Isco device, AcOEt/Cyclohexane) to afford 776 mg of a yellow oil. Yield=41%

It is assumed that the reaction mechanism includes the following steps:

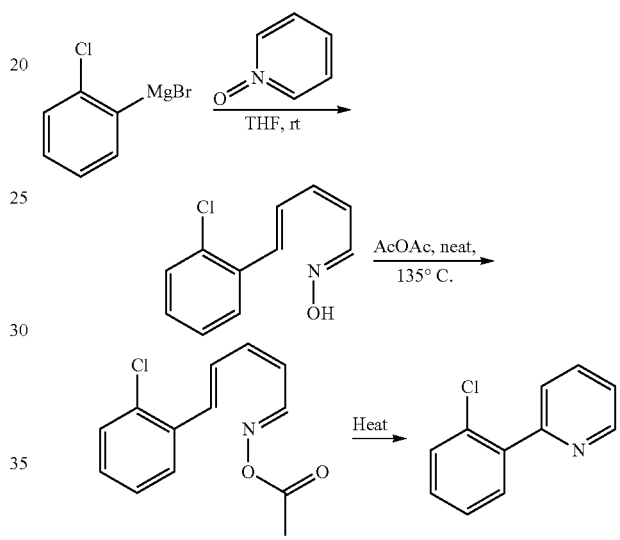

The following synthesis steps to yield Vismodegib are described above.

III. Synthesis According to Route C

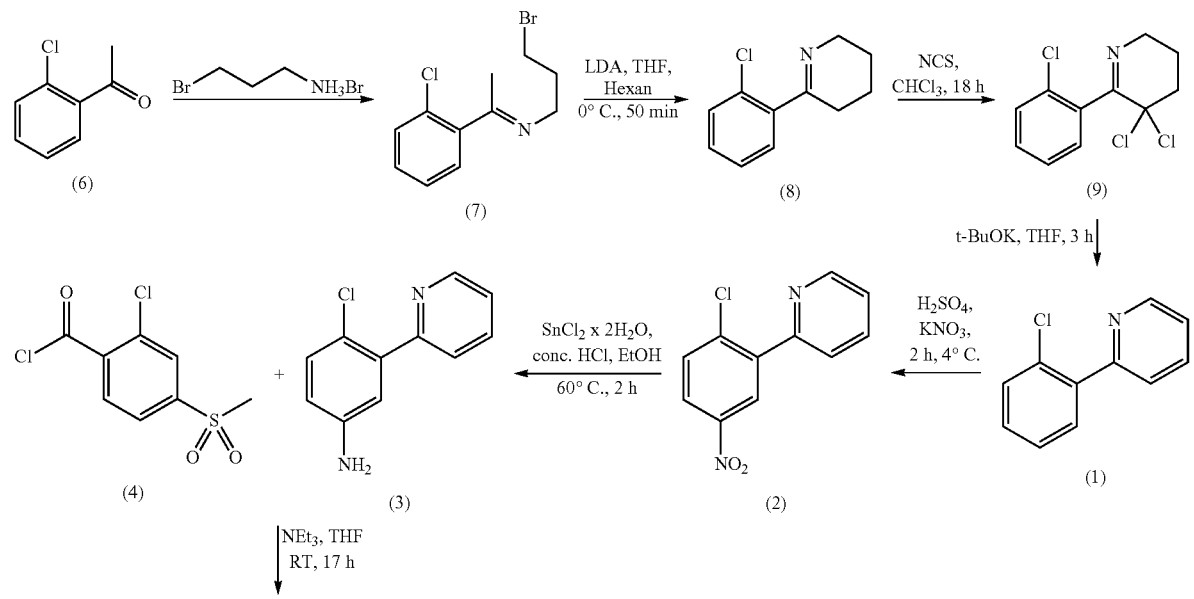

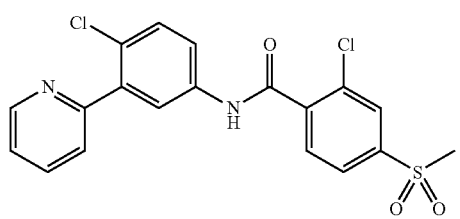

(5)
Vismodegib

Intermediate 7

Under nitrogen, at room temperature, to a solution of 2'-chloroacetophenone (1550 mg, 9.73 mmol) (6) and 3-bromopropylamine hydrobromide (2850 mg, 13.28 mmol) in a mixture of both dry DMF (10 mL) and DCM (3 mL), was added dropwise a solution of triethylamine (11.26 mL, 80.20 mmol) in DCM (10 mL) while vigorously stirring. Then the mixture was cooled to 0° C. and a solution of TiCl$_4$ (1.00 mL, 9.00 mmol) was added dropwise. The reaction suspension was vigorously stirred at room temperature overnight. The reaction mixture was diluted with diethyl ether (40 mL) and filtered to remove the solid formed. The latter was then washed with further diethyl ether (20 mL×2). The filtrate was washed with ice cold brine (20 mL×4) and dried over anhydrous MgSO$_4$. The removal of the volatiles yielded 2320 mg (8.45 mmol) of a brown oil. (Yield=87.0% yield).

Intermediate 8

Under nitrogen, to a solution of (E-Z)—N-(3-bromopropyl)-1-(2-chlorophenyl)ethan-1-imine (2320 mg, 8.45 mmol) (7) in dry THF (20 mL) at 0° C., was added dropwise a THF/Hexane 1.0 M solution of lithium diisopropylamide (10 mmol, 10 mL). After 50 minutes at 0° C., the reaction was quenched with NaHCO$_3$ (40 mL) and the phases were separated. The aqueous one was extracted with diethyl ether (40 mL×2) and the organic phases were reunited and dried over MgSO$_4$. The evaporation of the volatiles yielded 1530 mg (7.90 mmol) of an orange oil. Yield=79%

The other synthesis steps are the same as already described for Route A.

III. Synthesis According to a Route D

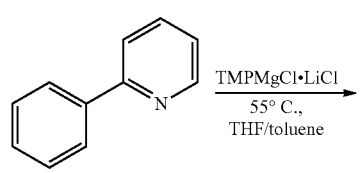

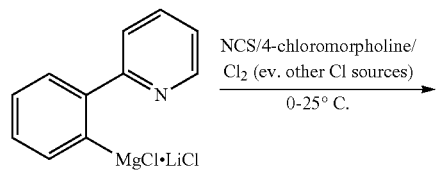

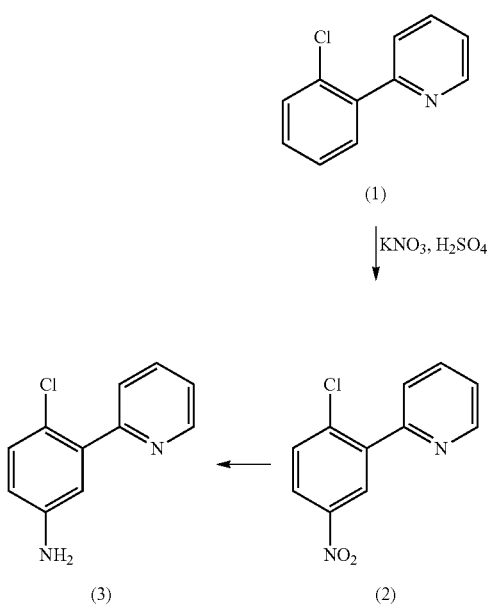

Grignard Preparation

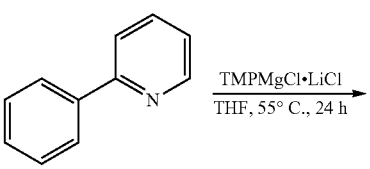

A solution of TMPMgCl.LiCl (1 M in THF/toluene, 6.44 ml, 6.44 mmol, 2 eq.) was loaded in an oven-dried Schlenk flask under nitrogen atmosphere. The solution was cooled in an ice bath and 2-Phenylpyridine (500 mg, 3.22 mmol) was added dropwise. Thereafter, the ice bath was removed and the mixture was heated to 55° C. and stirred for 24 hours. GC-MS yield 60% (quenched with I$_2$).

Intermediate (1)—Alternative A

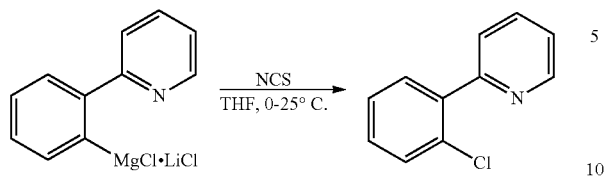

N-Chlorosuccinimide (640.8 mg, 4.8 mmol) was loaded in an oven-dried Schlenk flask under nitrogen atmosphere. The flask was cooled in an ice bath and 2 ml of (2-(pyridin-2-yl)phenyl)magnesium chloride lithium chloride complex solution was added dropwise (approx. 1.6 mmol). The mixture was stirred at 0° C. for 15 minutes and afterwards at room temperature.

Intermediate (1)—Alternative B

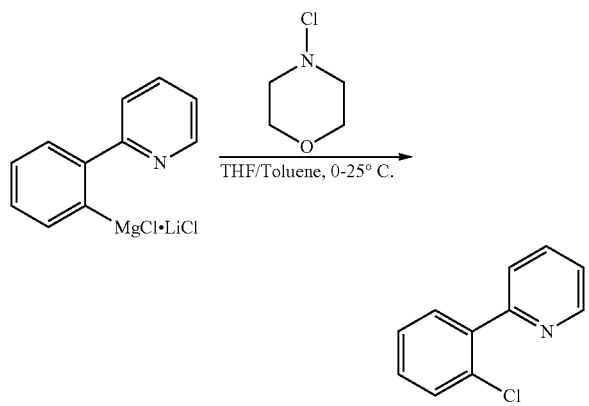

4-Chloromorpholine (5893.5 mg, 4.8 mmol) was loaded in an oven-dried Schlenk flask under nitrogen atmosphere. The flask was cooled in an ice bath and 2 ml of (2-(pyridin-2-yl)phenyl)magnesium chloride lithium chloride complex solution was added dropwise (approx. 1.6 mmol). The mixture was stirred at 0° C. for 15 minutes and afterwards at room temperature.

Intermediate 1—Alternative C

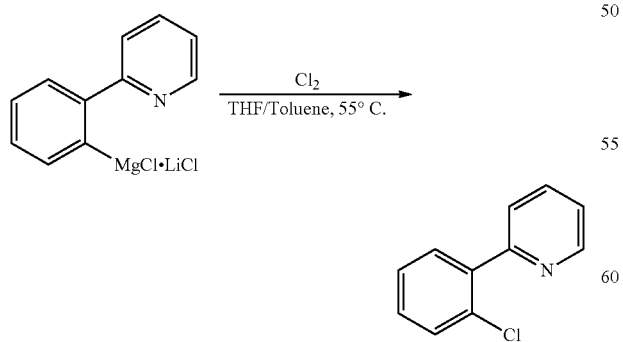

Through a dropping funnel, hydrochloric acid (1 M) was added dropwise into a Schlenk flask containing calcium hypochlorite (1.5 g). By means of vacuum, the released Cl$_2$ was drawn into a connected Schlenk flask. Thereafter, the Cl$_2$ gas was drawn up with a syringe and introduced into the Grignard solution.

III. Synthesis According to Route E

Synthesis of 1-(3-Brom-4-chlorphenyl)-2,2,5,5-tetramethyl-1,2,5-azadisilolidin

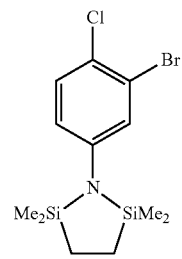

In a glove box: in a 250 mL Young Schlenk, to a solution of 3-bromo-4-chloroaniline (10.0 g, 48.4 mmol) in CH$_2$Cl$_2$ (100 mL), was added DMAP (598 mg, 4.8 mmol) followed by Et$_3$N (9.82 g, 96.9 mmol). Then a solution of chlorosilane (10.5 g, 48.4 mmol) in CH$_2$Cl$_2$ (40 mL) was added dropwise. The mixture was stirred at room temperature for 4 hours and then the triethylamine hydrochloride salts were precipitated adding 100 mL of n-pentane. The Precipitate was separated by filtration the suspension through a glass fit and the filtrate was concentrated reduced at pressure to obtain 16.7 g (47.9 mmol) of the title compound as an orange oil. Yield=quantitative. (MW=348.82) $^1$H-NMR (500 MHz, CD$_2$Cl$_2$), δ(ppm): 7.25 (d, J (Hz)=8.7, 1H); 7.16 (d, J (Hz)=2.7, $^1$H); 6.80 (dd, J (Hz)=8.7, 2.7, 1H); 0.88 (s, 4H); 0.21 (s, 12H). $^{13}$C{$^1$H}-NMR (125 MHz, CD2Cl2), δ(ppm): 148.6; 130.6; 128.6; 125.9; 124.4; 122.6; 8.7; 0.0. GC/EI-MS (Rt=5.42 min): 349/347 [M+1], 334/332 [M-CH$_3$]$^+$, 253, 73.

This compound may be further reacted to yield Vismodegib as described for Route A above.

What is claimed:

1. A process for the preparation of Vismodegib (2-chloro-N-(4-chloro-3-(pyridin-2-yl)phenyl)-4-(methylsulfonyl)-benzamide) wherein the process at least comprises the steps of
    reacting compound (1) (2-(2-chlorophenyl)pyridine) in the presence of nitric acid to give compound (2) (2-(2-chloro-5-nitrophenyl)pyridine),

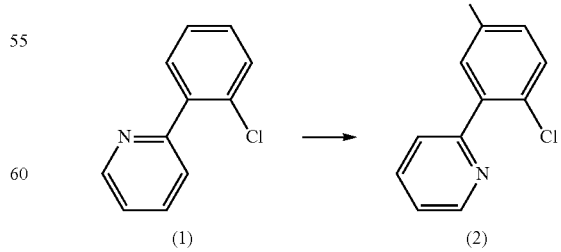

reducing compound (2) (2-(2-chloro-5-nitrophenyl)pyridine) to give compound (3) (4-chloro-3-(pyridin-2-yl) aniline)

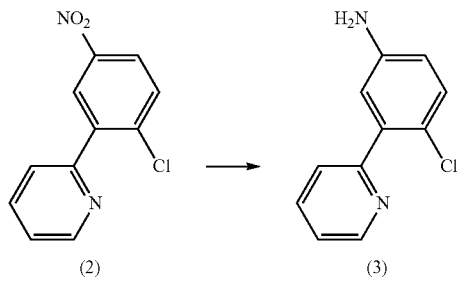 [SMILES: O=[N+]([O-])c1ccc(Cl)c(-c2ccccn2)c1 ; Nc1ccc(Cl)c(-c2ccccn2)c1]

and reacting compound (3) (4-chloro-3-(pyridin-2-yl)aniline) and compound (4) (2-chloro-4-(methylsulfonyl)benzoyl chloride) to give compound (5) (Vismodegib),

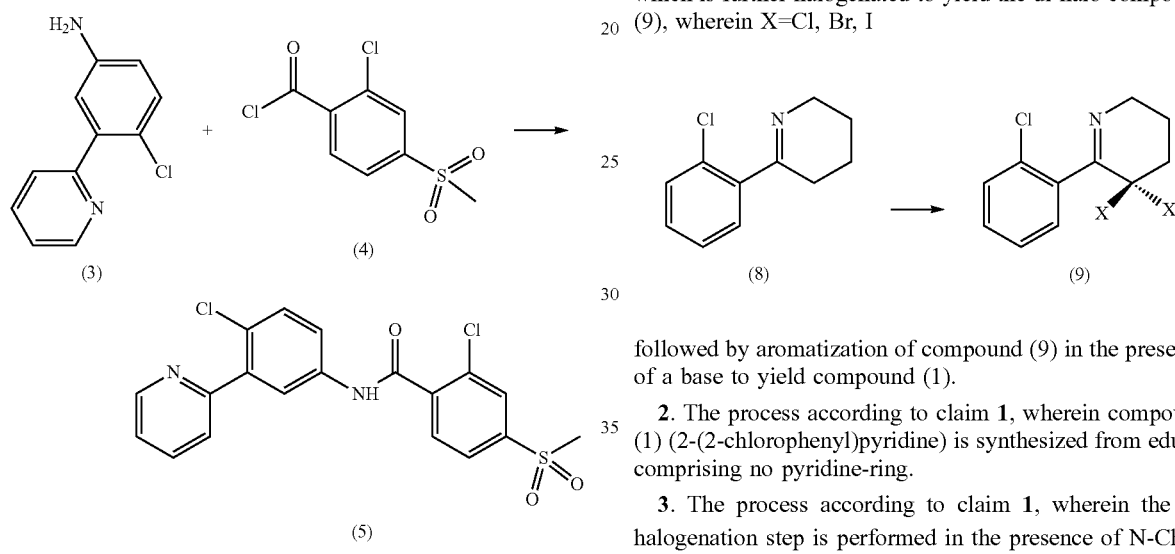

wherein compound (1) (2-(2-chlorophenyl)pyridine) is obtained by reacting compound (10) ((2-chloro-phenyl)-M-bromide), wherein M is Mg or Ca, and compound (11) (N-protected delta-Valerolactam), wherein L is a protection group to give compound (12) (5-L-amino-1-(2-chlorophenyl)pentan-1-one)

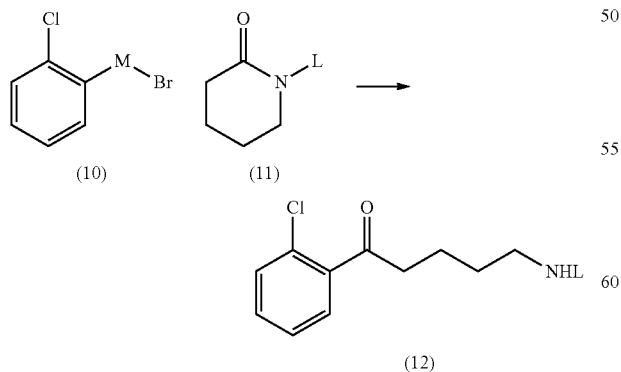

followed by de-protection of compound (12) to give bi-cyclic compound (8)

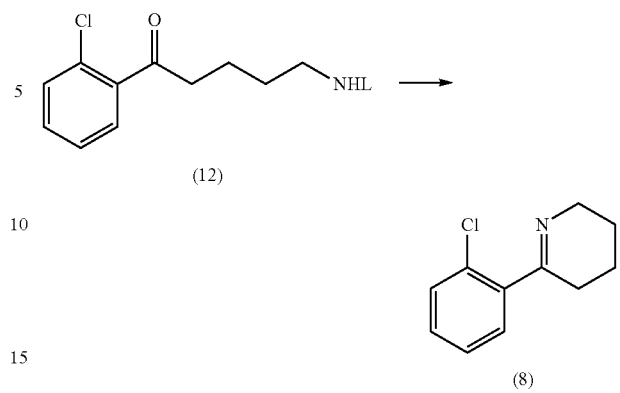

which is further halogenated to yield the di-halo compound (9), wherein X=Cl, Br, I followed by aromatization of compound (9) in the presence of a base to yield compound (1).

2. The process according to claim 1, wherein compound (1) (2-(2-chlorophenyl)pyridine) is synthesized from educts comprising no pyridine-ring.

3. The process according to claim 1, wherein the di-halogenation step is performed in the presence of N-Chlorosuccinimide (NCS) and the molar ratio of the NCS to the educt (NCS:educt) is larger or equal to 4.

4. A process for the preparation of Vismodegib (2-chloro-N-(4-chloro-3-(pyridin-2-yl)phenyl)-4-(methylsulfonyl)-benzamide) wherein the process at least comprises the steps of reacting compound (1) (2-(2-chlorophenyl)pyridine) in the presence of nitric acid to give compound (2) (2-(2-chloro-5-nitrophenyl)pyridine),

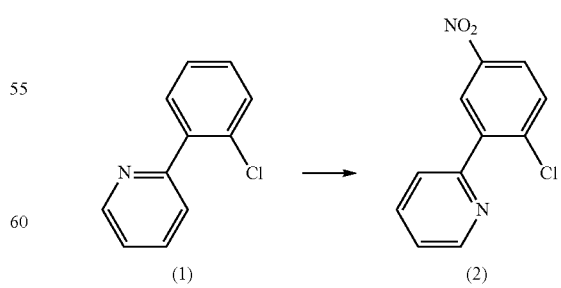

reducing compound (2) (2-(2-chloro-5-nitrophenyl)pyridine) to give compound (3) (4-chloro-3-(pyridin-2-yl)aniline)

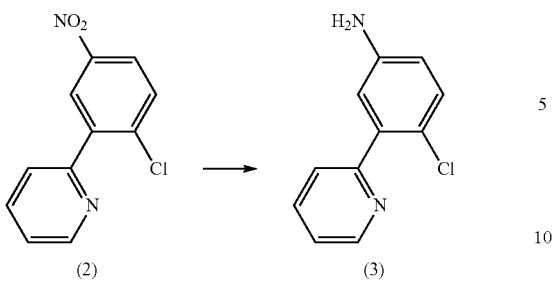

and reacting compound (3) (4-chloro-3-(pyridin-2-yl)aniline) and compound (4) (2-chloro-4-(methylsulfonyl)benzoyl chloride) to give compound (5) (Vismodegib)

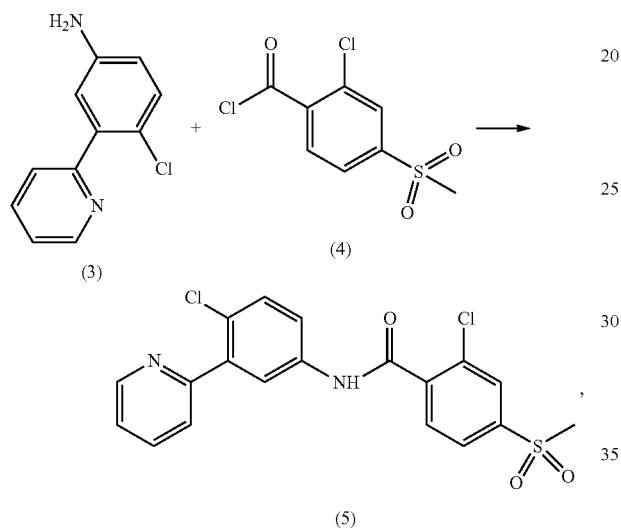

wherein compound (1) (2-(2-chlorophenyl)pyridine) is synthesized from at least one educt comprising a pyridine-ring, wherein compound (1) (2-(2-chlorophenyl)pyridine) is obtained by reacting compound (13) ((2-chlorophenyl)magnesiumbromide) and compound (14) (pyridine N-oxide) to yield compound (1)

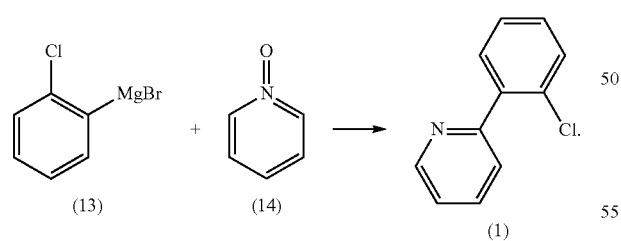

5. The process according to claim 4, wherein the reaction is performed in boiling acetic acid anhydride $(Ac)_2O$.

6. A process for the preparation of Vismodegib (2-chloro-N-(4-chloro-3-(pyridin-2-yl)phenyl)-4-(methylsulfonyl)-benzamide) wherein the process at least comprises the steps of reacting compound (1) (2-(2-chlorophenyl)pyridine) in the presence of nitric acid to give compound (2) (2-(2-chloro-5-nitrophenyl)pyridine),

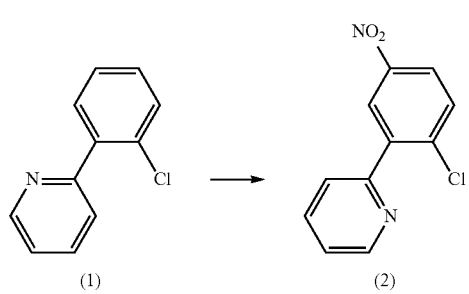 [SMILES: Clc1ccccc1-c1ccccn1 ; O=[N+]([O-])c1ccc(Cl)c(-c2ccccn2)c1]

reducing compound (2) (2-(2-chloro-5-nitrophenyl)pyridine) to give compound (3) (4-chloro-3-(pyridin-2-yl)aniline)

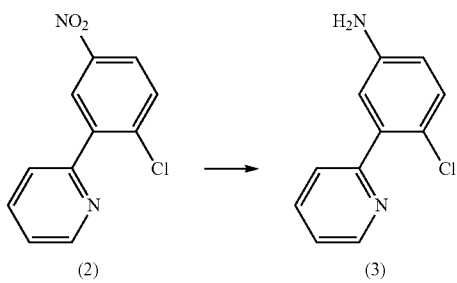 [SMILES: O=[N+]([O-])c1ccc(Cl)c(-c2ccccn2)c1 ; Nc1ccc(Cl)c(-c2ccccn2)c1]

and reacting compound (3) (4-chloro-3-(pyridin-2-yl)aniline) and compound (4) (2-chloro-4-(methylsulfonyl)benzoyl chloride) to give compound (5) (Vismodegib)

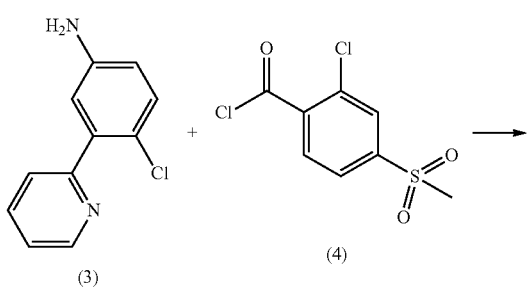

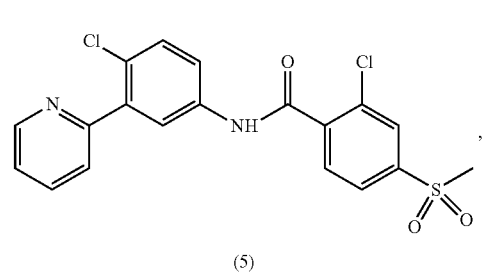

wherein compound (1) (2-(2-chlorophenyl)pyridine) is synthesized from at least one educt comprising a pyridine-ring, wherein compound (1) (2-(2-chlorophenyl)pyridine) is obtained by reacting compound (15) (2-phenylpyridine) in the presence of a Grignard-reagent to yield compound (16) (2-(2-Magnesiumchlorophenyl)pyridine)

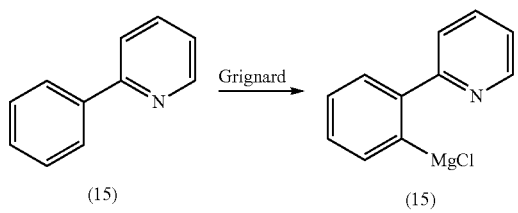

(15) → (15)

and further reacting compound (16) in the presence of a chloride-source to yield compound (1)

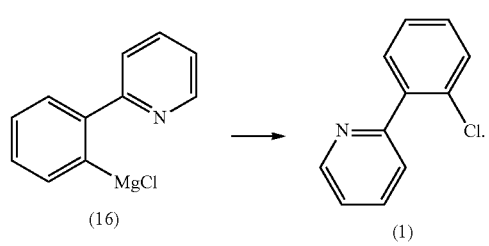

(16) → (1)

7. The process according to claim 6, wherein the Grignard-reagent is 2,2,6,6-Tetramethylpiperidinylmagnesium chloride lithium chloride.

8. A process for the preparation of Vismodegib (2-chloro-N-(4-chloro-3-(pyridin-2-yl)phenyl)-4-(methylsulfonyl)-benzamide) wherein the process at least comprises the steps of reacting compound (1) (2-(2-chlorophenyl)pyridine) in the presence of nitric acid to give compound (2) (2-(2-chloro-5-nitrophenyl)pyridine),

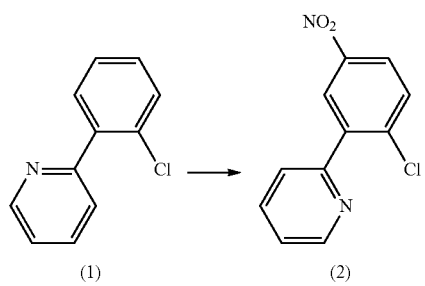 [SMILES: Clc1ccccc1-c1ccccn1 ; O=[N+]([O-])c1ccc(Cl)c(-c2ccccn2)c1]

(1) → (2)

reducing compound (2) (2-(2-chloro-5-nitrophenyl)pyridine) to give compound (3) (4-chloro-3-(pyridin-2-yl) aniline)

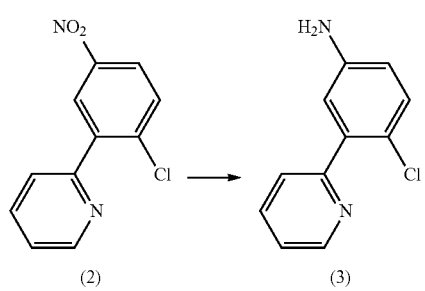

(2) → (3)

and reacting compound (3) (4-chloro-3-(pyridin-2-yl)aniline) and compound (4) (2-chloro-4-(methylsulfonyl)benzoyl chloride) to give compound (5) (Vismodegib)

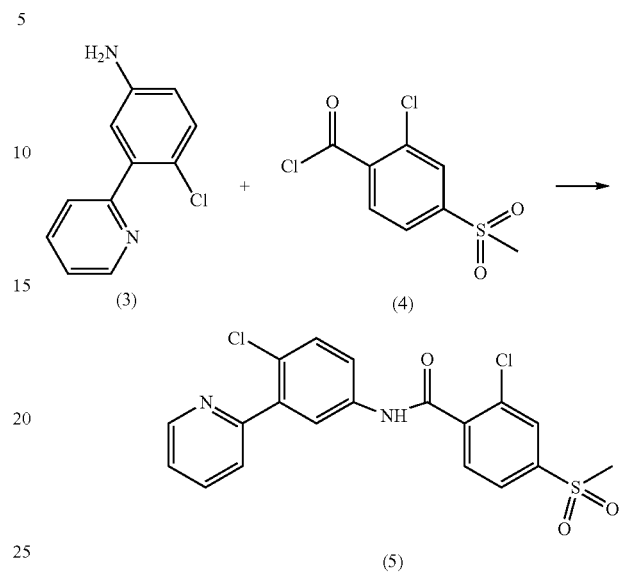

(3) + (4) → (5)

wherein compound (1) (2-(2-chlorophenyl)pyridine) is obtained by reacting compound (6) (2-chloroacetophenone) and 3-Y-propylamine, wherein Y is selected from the group consisting of halogen, OH, SH, $NH_2$, $NR_2$, $PR_2$, wherein R is an alkyl moiety, to yield the acyclic imine compound (7)

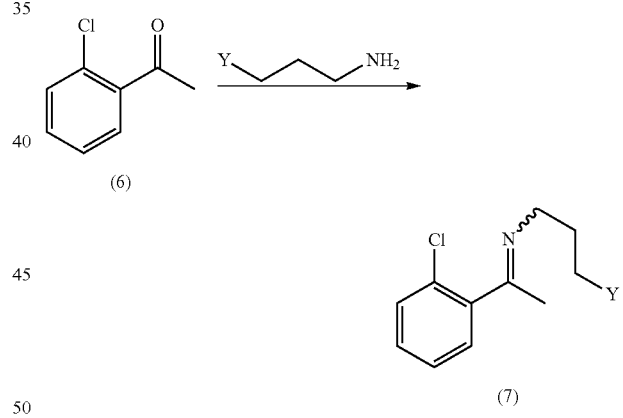

(6) → (7)

followed by a reaction in the presence of a base to yield the cyclic imine compound (8)

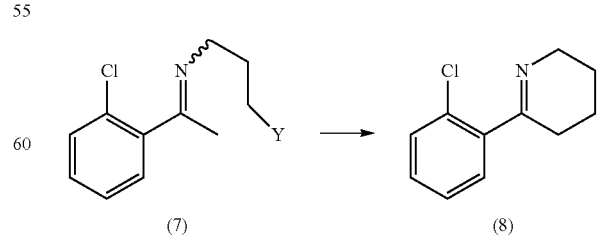

(7) → (8)

and halogenating compound (8) to yield the di-halo compound (9), wherein X=Cl, Br, I

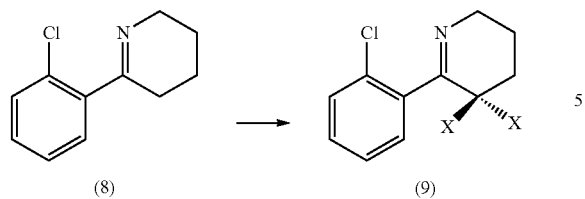

followed by aromatization in the presence of a base to yield compound (1), wherein the first reaction step is performed in the presence of dimethylformamide (DMF), dichloromethane (DCM), $TiCl_4$ and trimethylamine ($Et_3N$).

9. The process according to claim 8, wherein the aromatization step is performed in the presence of a polar aprotic solvent and a base, wherein the base is selected from the group consisting of potassium bis(trimethylsilyl)amide, lithium diisopropylamide (LDA), caesium carbonate, caesium bicarbonate, potassium carbonate, sodium carbonate, potassium bicarbonate, sodium bicarbonate, t-BuOK or mixtures thereof.

* * * * *